United States Patent
Ochiai et al.

(10) Patent No.: US 12,220,506 B2
(45) Date of Patent: Feb. 11, 2025

(54) BREAST PUMP

(71) Applicant: PIGEON CORPORATION, Tokyo (JP)

(72) Inventors: Yukifumi Ochiai, Tokyo (JP); Sumiko Kuroishi, Tokyo (JP)

(73) Assignee: PIGEON CORPORATION, Tokyo (JP)

( * ) Notice: Subject to any disclaimer, the term of this patent is extended or adjusted under 35 U.S.C. 154(b) by 1049 days.

(21) Appl. No.: 15/734,333

(22) PCT Filed: Jun. 3, 2019

(86) PCT No.: PCT/JP2019/022015
§ 371 (c)(1),
(2) Date: Dec. 2, 2020

(87) PCT Pub. No.: WO2019/235432
PCT Pub. Date: Dec. 12, 2019

(65) Prior Publication Data
US 2021/0220535 A1  Jul. 22, 2021

(30) Foreign Application Priority Data
Jun. 5, 2018  (JP) .................................. 2018-107991

(51) Int. Cl.
*A61M 1/06* (2006.01)
(52) U.S. Cl.
CPC ............. *A61M 1/064* (2014.02); *A61M 1/06* (2013.01); *A61M 1/0697* (2021.05)
(58) Field of Classification Search
CPC ........ A61M 1/06; A61M 1/062; A61M 1/064; A61M 1/066; A61M 1/0697
See application file for complete search history.

(56) References Cited

U.S. PATENT DOCUMENTS 5,885,246 A * 3/1999 Ford ..................... A61M 1/066
604/74
6,579,258 B1 * 6/2003 Atkin .................... A61M 1/066
604/74
(Continued)

FOREIGN PATENT DOCUMENTS

CN        204637098 U       9/2015
CN        105477704 A       4/2016
(Continued)

OTHER PUBLICATIONS

International Search Report of PCT/JP2019/022015 mailed Jul. 30, 2019.
(Continued)

*Primary Examiner* — Quynh-Nhu H. Vu
(74) *Attorney, Agent, or Firm* — Muncy, Geissler, Olds & Lowe, P.C.

(57) ABSTRACT

Breast pump 2 includes breast pump main body 3 generating a negative pressure for pumping, hood 4 connected to the main body 3 and placed onto a breast, and buffer portion 7 mounted detachably to hood 4, and made of a material softer than a material of hood 4. Hood 4 includes flow path portion 41 connected to the main body 3 and through which breast milk extracted from the breast passes, and diameter expansion portion 42 having a diameter expanding from flow path portion 41 toward edge portion 43 on a side opposite to flow path portion 41. Buffer portion 7 includes bonding portion 71 fitted to edge portion 43, and sealing portion 72 provided on the side opposite to bonding portion 71 and comes into close contact with inner surface 421 of diameter expansion portion 42 between flow path portion 41 and edge portion 43.

16 Claims, 6 Drawing Sheets

(56) References Cited

U.S. PATENT DOCUMENTS

| | | | | |
|---|---|---|---|---|
| 7,766,865 B2 * | 8/2010 | Rollin | A61M 1/066 | 604/74 |
| 8,523,804 B2 * | 9/2013 | Cudworth | A61M 1/0697 | 604/74 |
| 8,608,685 B2 * | 12/2013 | Tashiro | A61M 1/06 | 604/74 |
| 9,011,372 B2 * | 4/2015 | Jones | A61M 1/06 | 604/74 |
| 9,044,534 B2 * | 6/2015 | Behrens | A61M 1/82 | |
| 9,265,869 B2 * | 2/2016 | Darnell | A61M 1/066 | |
| 2004/0029486 A1 * | 2/2004 | Greter | A61M 1/066 | 604/74 |
| 2004/0127845 A1 * | 7/2004 | Renz | A61M 1/06935 | 604/74 |
| 2005/0256449 A1 * | 11/2005 | Tashiro | A61M 1/066 | 604/74 |
| 2006/0106334 A1 * | 5/2006 | Jordan | A61M 1/062 | 604/74 |
| 2007/0060873 A1 * | 3/2007 | Hiraoka | A61M 1/82 | 604/74 |
| 2007/0078383 A1 * | 4/2007 | Tashiro | A61M 1/81 | 604/74 |
| 2008/0195039 A1 * | 8/2008 | Kataoka | A61M 1/06 | 604/74 |
| 2008/0208115 A1 * | 8/2008 | Kliegman | A61M 1/0697 | 604/74 |
| 2010/0324477 A1 | 12/2010 | Paterson | | |
| 2012/0004604 A1 * | 1/2012 | Van Der Kamp | A61M 1/06 | 604/74 |
| 2020/0171223 A1 * | 6/2020 | Ochiai | A61M 1/064 | |
| 2021/0213184 A1 * | 7/2021 | Ochiai | A61M 1/06 | |

FOREIGN PATENT DOCUMENTS

| | | |
|---|---|---|
| GB | 2380411 A | 4/2003 |
| JP | 2007-075293 A | 3/2007 |
| JP | 2012-231904 A | 11/2012 |
| WO | 2005/084729 A1 | 9/2005 |
| WO | 2007/017968 A1 | 2/2007 |

OTHER PUBLICATIONS

Written Opinion of PCT/JP2019/022015 mailed Jul. 30, 2019.
Office Action of the corresponding CN application No. 201980037391.5 mailed Jul. 15, 2023 and English translation thereof.
Office action of the corresponding JP application No. 2018-107991 mailed Sep. 29, 2022 and English translation thereof.
The extended European search report for the corresponding EP application No. 19815110.2 mailed Jan. 21, 2022.

* cited by examiner

BREAST PUMP

TECHNICAL FIELD

The present invention relates to a breast pump that creates a negative pressure for pumping and sucks breast milk.

BACKGROUND ART

Conventionally, a breast pump for sucking breast milk of a user has been known. For example, PTL 1 discloses a breast pump including a storage container, a breast pump main body, a pumping diameter expansion portion, and a buffer portion. The pumping diameter expansion portion of the breast pump described PTL 1 is an expansion part that is brought into abutment with a breast of the user, and is provided in the breast pump main body. The buffer portion of the breast pump described in PTL 1 is formed in a substantially circular trumpet shape along an opening of the pumping diameter expansion portion, and is detachably disposed in the pumping diameter expansion portion. At least a part of the buffer portion is brought into abutment with the breast of the user.

The buffer portion of the breast pump described in PTL 1 is formed of an elastic body such as silicone rubber, and includes a through hole, an areola abutment portion, and a breast contact portion. The through hole exposes the nipple of the user in a state where the breast of the user is in abutment with the pumping diameter expansion portion. The areola abutment portion is a projection provided in the vicinity of the through hole or a protrusion concentric with the through hole, and comes into abutment with an areola portion of the user. The breast contact portion is a concentric protrusion provided outside the areola abutment portion, and is brought into close contact with the breast of the user. Such a buffer portion has a function of suppressing irritation and pain caused by the pumping diameter expansion portion coming into abutment with the breast, and a function of preventing a negative pressure generated in the pumping diameter expansion portion from leaking to the outside of the pumping diameter expansion portion.

CITATION LIST

Patent Literature

[PTL 1] Japanese Patent Application Publication No. 2012-231904

SUMMARY OF INVENTION

Technical Problem

The buffer portion disclosed in PTL 1 extends from an outer edge of the pumping diameter expansion portion to a pumping portion ventilation path of the pumping diameter expansion portion in a state of being mounted onto the pumping diameter expansion portion. Specifically, in a state in which the buffer portion is mounted on the pumping diameter expansion portion, a part of the through hole of the buffer portion is disposed in the pumping portion ventilation path corresponding to a back portion of the pumping diameter expansion portion. On the other hand, once the user inserts her breast into the pumping diameter expansion portion, the nipple of the user is positioned in the vicinity of the through hole of the buffer portion. Furthermore, the areola portion of the user comes into abutment with the areola abutment portion of the buffer portion. Therefore, the buffer portion disclosed in PTL 1 may be deformed by the negative pressure generated in the pumping diameter expansion portion during pumping, may rub against or pinch the nipple or the vicinity of or areola of the user. This may cause pain or discomfort to the user during pumping. In this regard, the buffer portion disclosed in PTL 1 has room for improvement.

Furthermore, as described above, the part of the through hole of the buffer portion is disposed in the pumping portion ventilation path corresponding to the back portion of the pumping diameter expansion portion. Therefore, when the user mounts the buffer portion to the pumping diameter expansion portion, occasionally a relatively large frictional force may be generated between the buffer portion and the pumping diameter expansion portion or the buffer portion may be caught on the outer edge of the pumping diameter expansion portion. As a result, it may take as longer time and more effort to mount the buffer portion onto the pumping expansion portion, or the buffer portion may not be mounted appropriately to the pumping diameter expansion portion. In a case where the buffer portion cannot appropriately mounted to the pumping diameter expansion portion, the adhesion of the buffer portion to the pumping diameter expansion portion is reduced, causing the negative pressure generated in the pumping diameter expansion portion to leak to the outside of the pumping diameter expansion portion. In this regard, the buffer portion disclosed in PTL 1 has room for improvement.

The present invention was contrived in order to solve the foregoing problems, and an object thereof is to provide a breast pump capable of not only reducing irritation and pain in a breast of a user but also improving the mountability of a buffer portion of the breast pump.

Solution to Problem

According to the present invention, the foregoing problems are solved by a breast pump including: a breast pump main body generating a negative pressure for pumping; a hood connected to the breast pump main body and placed onto a breast; and a buffer portion having a ring shape and mounted detachably to the hood, the buffer portion being made of a material softer than a material of the hood and having elasticity, wherein the hood includes a flow path portion which is connected to the breast pump main body and through which breast milk extracted from the breast passes, and a diameter expansion portion which has a diameter expanding from the flow path portion toward an edge portion on a side opposite to the flow path portion and which is placed onto the breast, and the buffer portion includes a bonding portion fitted to the edge portion, and a sealing portion which is provided on a side opposite to the bonding portion and comes into close contact with an inner surface of the diameter expansion portion between the flow path portion and the edge portion.

According to the breast pump of the present invention, the hood placed onto the breast is connected to the breast pump main body that generates a negative pressure for pumping, and has a flow path portion and a diameter expansion portion. The flow path portion is connected to the breast pump main body. The breast milk extracted from the breast of the user passes through the flow path portion. The diameter of the diameter expansion portion expands from the flow path portion toward the edge portion on the opposite side of the flow path portion. The diameter expansion portion is placed onto the breast of the user. Also, the buffer portion is in the shape of a ring, detachably mounted onto the hood, made of a material softer than the material of the hood, and therefore has elasticity. The buffer portion has a bonding portion fitted to the edge portion of the hood, and a sealing portion provided on a side opposite to the bonding portion. The sealing portion comes into close contact with an inner surface of the diameter expansion portion between the flow path portion of the hood and the edge portion of the hood.

Thus, instead of extending from the edge portion of the hood to the flow path portion, the buffer portion of the breast pump according to the present invention extends from the edge portion of the hood to a part between the edge portion of the hood and the flow path portion while being mounted to the hood. In other words, while the buffer portion is mounted to the hood, the sealing portion is disposed on a side of an opening as seen from the flow path portion, the opening having the breast inserted thereto. In this case, an edge portion of the opening corresponds to the edge portion of the hood. On the other hand, when the user inserts the breast into a space surrounded by the hood through the opening of the hood, the nipple of the user enters the flow path portion of the hood. Also, an areola portion of the user is disposed in the vicinity of a boundary portion between the flow path portion and the diameter expansion portion. Therefore, when inserting the breast into the hood or even when the buffer portion becomes deformed due to a negative pressure generated on the hood at the time of pumping, the buffer portion can be prevented from rubbing against or pinching the vicinity of the nipple or areola of the user. Thus, the breast pump according to the present invention can reduce irritation and pain in the nipple and areola of the user.

Furthermore, as described above, instead of extending from the edge portion of the hood to the flow path portion, the buffer portion extends from the edge portion of the hood to the part between the edge portion of the hood and the flow path portion while being mounted to the hood. Therefore, when the user mounts the buffer portion onto the hood, not only is it possible to reduce the frictional force generated between the buffer portion and the hood, but also the buffer portion can be prevented from getting caught on the edge portion of the hood. As a result, it does not take a lot of time and effort to mount the buffer portion to the hood, and inappropriate mounting of the buffer portion to the hood can be prevented. Thus, the breast pump according to the present invention can prevent the negative pressure generated in the hood from leaking to the outside of the hood, by improving the mountability of the buffer portion.

In the breast pump according to the present invention, it is preferred that an outer diameter of a tip of the sealing portion be larger than an inner diameter of a part of the diameter expansion portion with which the tip of the sealing portion comes into contact.

According to the breast pump of the present invention, in the state where the buffer portion is mounted to the hood, a force in a direction perpendicular to the inner surface of the diameter expansion portion is applied from the sealing portion to the diameter expansion portion. Specifically, since the outer diameter of the tip of the sealing portion is larger than the inner diameter of the part of the diameter expansion portion with which the tip of the sealing portion comes into contact, virtually the tip of the sealing portion bites into the part of the diameter expansion portion with which the tip of the sealing portion comes into contact. On the other hand, since the material of the buffer portion is softer than the material of the hood, in reality the tip of the sealing portion cannot bite into the part of the diameter expansion portion with which the tip of the sealing portion comes into contact.

Consequently, the tip of the sealing portion tries to deform toward the inside of the diameter expansion portion. At this moment, since the buffer portion has elasticity, when the tip of the sealing portion is compressed and tries to deform toward the inside of the diameter expansion portion, the force generated inside the tip part of the sealing portion becomes dispersed throughout the entire tip part of the sealing portion. Therefore, the tip part of the sealing portion can apply a force toward the inner surface of the diameter expansion portion, while having the occurrence of wrinkles in the tip part prevented. Consequently, in the state where the buffer portion is mounted to the hood, the force in the direction perpendicular to the inner surface of the diameter expansion portion is applied from the sealing portion to the diameter expansion portion. As a result, the adhesion between the sealing portion and the diameter expansion portion can be improved, thereby preventing the breast milk from entering between the sealing portion and the diameter expansion portion.

In the breast pump according to the present invention, it is preferred that the buffer portion further include a cushion portion which, between the bonding portion and the sealing portion, protrudes from the diameter expansion portion toward the inside of the diameter expansion portion and is positioned away from the inner surface of the diameter expansion portion.

According to the breast pump of the present invention, the cushion portion provided between the bonding portion and the sealing portion protrudes from the diameter expansion portion toward the inside of the diameter expansion portion, away from the inner surface of the diameter expansion portion. Therefore, a space is provided between the cushion portion and the diameter expansion portion. This space can function as an air cushion. The cushion portion, therefore, is capable of not only fitting gently to the breast of the user to ensure comfortable skin contact but also ensuring the airtightness of the space surrounded by the breast, the buffer portion, and the hood.

In the breast pump according to the present invention, it is preferred that the buffer portion further include a bending portion provided at a boundary between the cushion portion and the sealing portion, the bending portion being configured to bend when the cushion portion is deformed, thereby preventing the deformation of the cushion portion from being transmitted to the sealing portion.

According to the breast pump of the present invention, the bending portion provided at the boundary between the cushion portion and the sealing portion is configured to bend when the cushion portion is deformed, to prevent the deformation of the cushion portion from being transmitted to the sealing portion. Specifically, when the breast is inserted into the hood and comes into contact with the cushion portion, the cushion portion becomes deformed and then collapses. At this moment, the bending portion provided at the boundary between the cushion portion and the sealing portion bends, to prevent the deformation of the cushion portion from being transmitted to the sealing portion. Therefore, even when the cushion portion is deformed, the bending portion prevents the sealing portion from becoming deformed or floating from the diameter expansion portion, thereby ensuring the adhesion between the sealing portion and the diameter expansion portion.

In the breast pump according to the present invention, it is preferred that a thickness of the bonding portion be greater than a thickness of the sealing portion.

According to the breast pump of the present invention, the rigidity of the bonding portion can be increased. Therefore, the user can easily mount the buffer portion onto the hood.

Advantageous Effects of Invention

The present invention can provide a breast pump capable of not only reducing irritation and pain in the breast of the user but also improving the mountability of the buffer portion.

DESCRIPTION OF EMBODIMENTS

Figure 1:
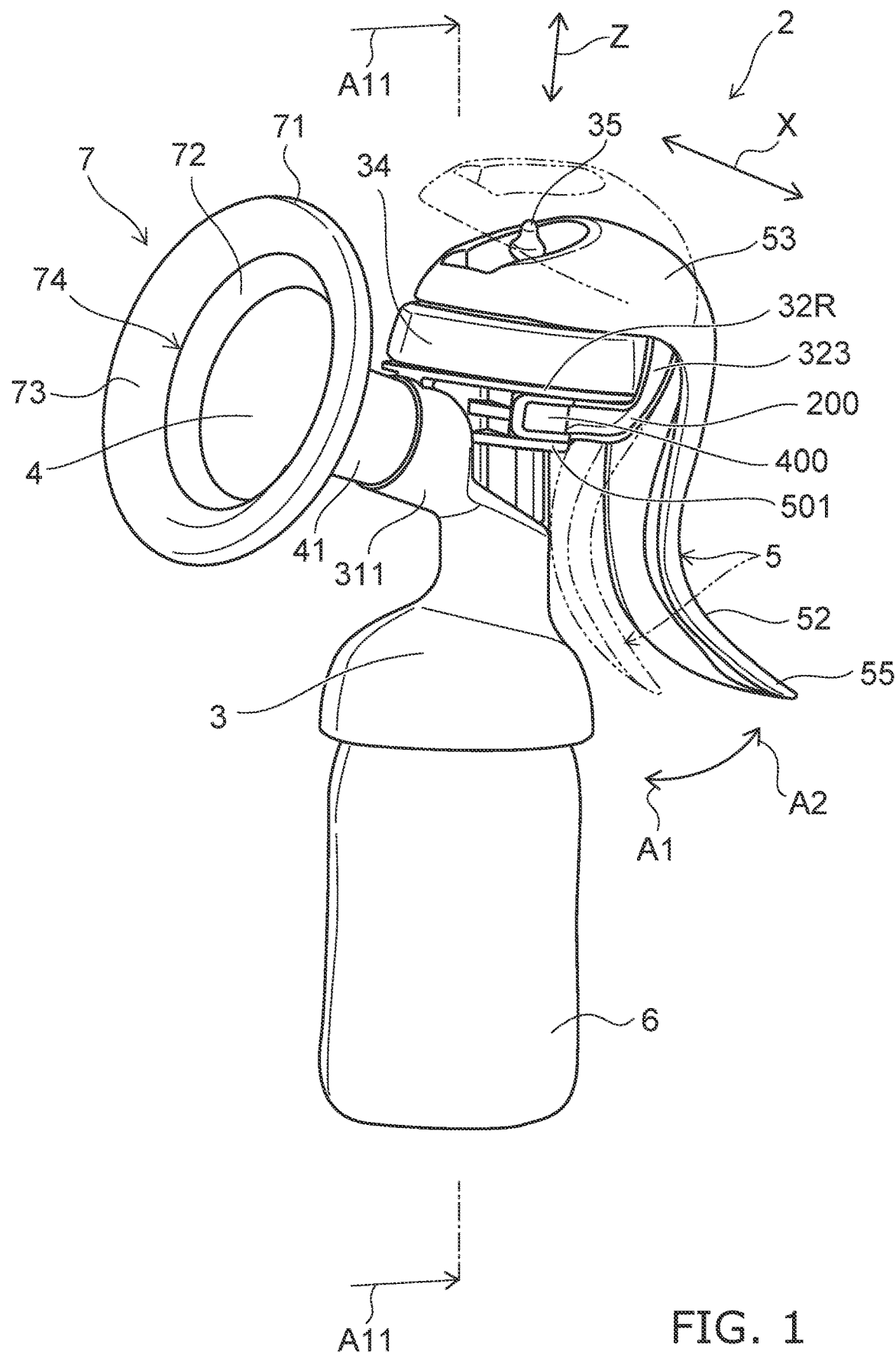
FIG. 1 is a perspective view showing a breast pump according to an embodiment of the present invention.

Preferred embodiments of the present invention are now described hereinafter in detail with reference to the drawings.

Note that, since the embodiments described below are favorable specific examples of the present invention, various technically favorable limits are applied thereto; however, the scope of the present invention is not limited to these embodiments unless the following description states that the present invention is particularly limited. Further, in each drawing, identical components are designated the same reference numerals; thus, detailed descriptions thereof are omitted accordingly.

Figure 2:
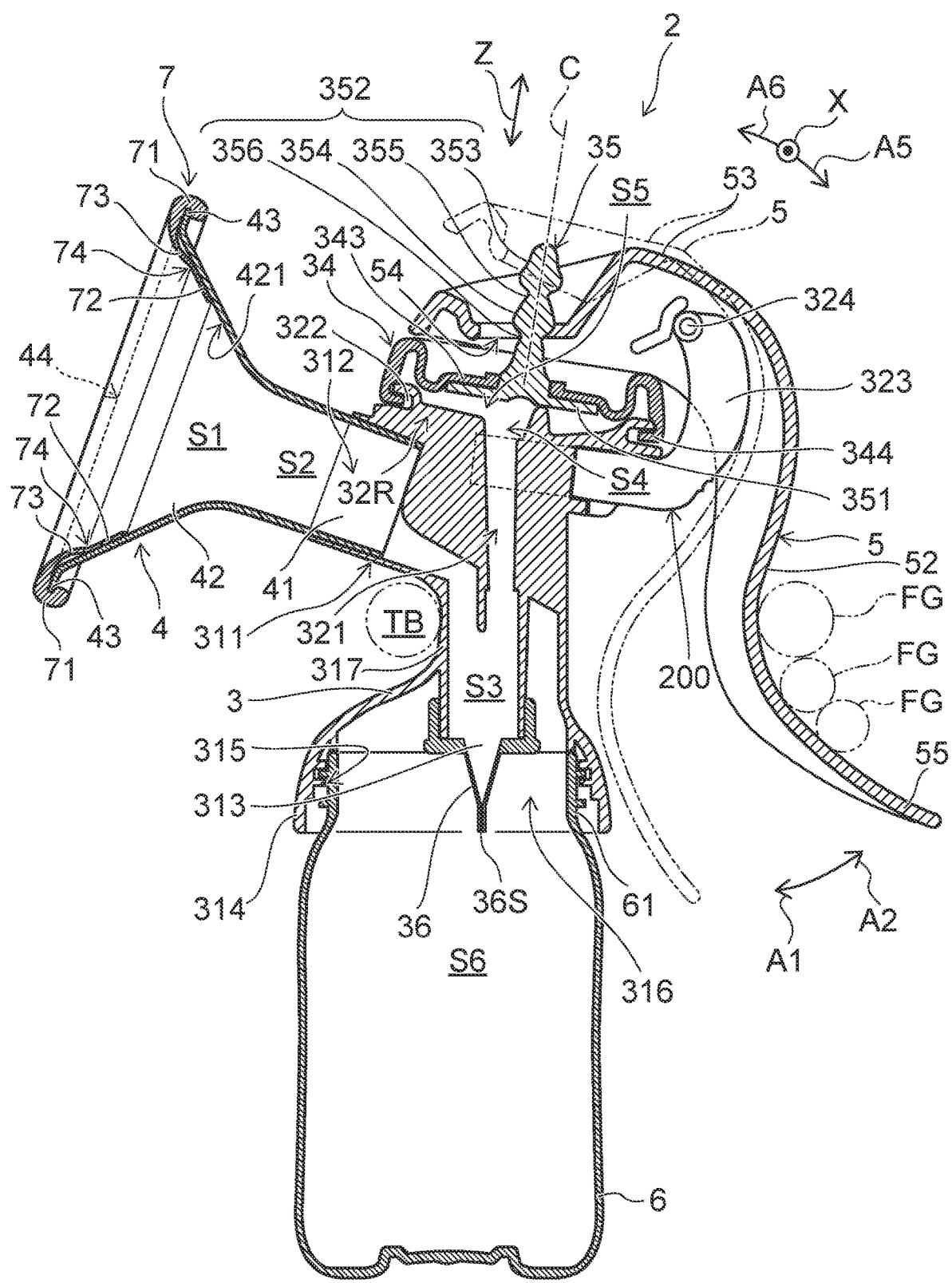
FIG. 2 is a cross-sectional view of the breast pump according to the present embodiment, taken along a cut section A11-A11 shown in FIG. 1.
Figure 3:
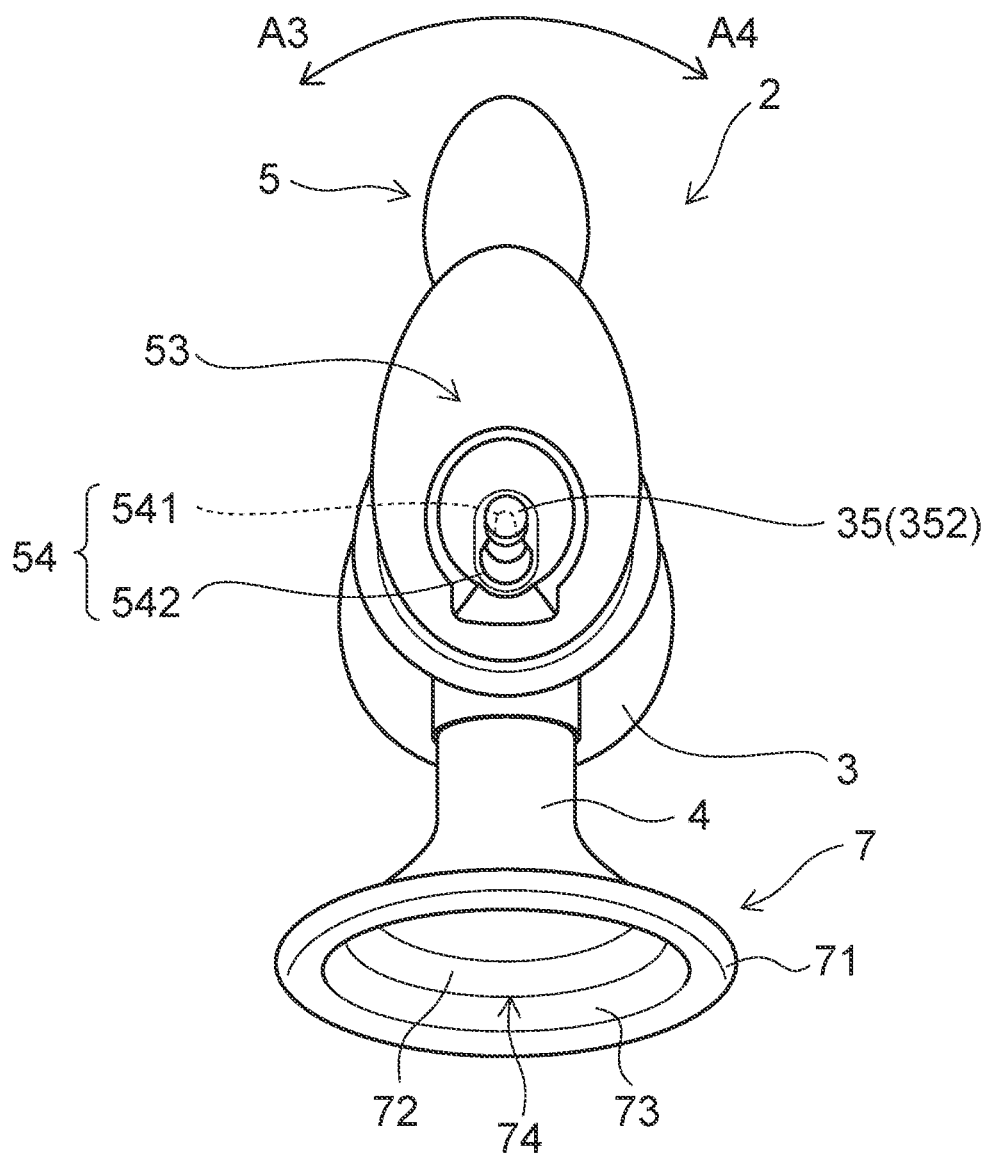
FIG. 3 is a plan view showing the breast pump according to the present embodiment from above.

A breast pump according to the present embodiment is now described with reference to FIGS. 1 to 3. A breast pump 2 according to the present embodiment is a tool that can be operated by a user to extract breast milk, and is used when breast-feeding an infant directly is difficult or a nipple is damaged, or for the purpose of preventing mastitis. The breast pump 2 shown in FIGS. 1 to 3 is a manual breast pump that can be operated manually by the user to extract breast milk. It should be noted that the breast pump according to the present embodiment is not limited to a manual breast pump and may be an electric breast pump that electrically obtains power required for a pumping operation. An example in which the breast pump is a manual pump is described hereinafter.

As shown in FIGS. 1 and 2, the breast pump 2 includes a breast pump main body 3, a hood 4, and a buffer portion 7. The breast pump 2 may also include a diaphragm 34, a handle 5, a holding member 200, and a bottle 6.

The breast pump main body 3 is relatively light, and is molded with a hard synthetic resin material. Examples of the material of the breast pump main body 3 include polypropylene, polycarbonate, polycicloolefin, polyethersulfone, and polyphenylsulfone. A first passage 312 through which air and extracted breast milk pass is formed inside the mounting portion 311 to which the hood 4 is mounted. As shown in FIG. 2, the first passage 312 is spatially connected to a communication portion S4 via an internal space S3 and a second passage 321 formed substantially in the middle of the breast pump main body 3, the communication portion S4 being formed in an upper portion of the breast pump main body 3. The internal space S3 is a breast milk storage space for temporarily storing the extracted breast milk.

The upper portion of the breast pump main body 3 is provided with the diaphragm 34 in a detachable manner. The diaphragm 34 is integrally molded with an elastic body such as a synthetic resin, and therefore has flexibility as a whole. A lower end portion 344 of the diaphragm 34 is attached to cover an outer periphery of a substantially disk-shaped diaphragm mounting portion 32R provided in the upper portion of the breast pump main body 3. Specifically, the diaphragm 34 is mounted above the diaphragm mounting portion 32R of the breast pump main body 3.

A negative pressure space S5 formed between the breast pump main body 3 and the diaphragm 34 is a region (space) where a negative pressure is applied. As a result of the diaphragm 34 changing the shape thereof along an axis C, the negative pressure space S5 formed between the breast pump main body 3 and the diaphragm 34 enters a negative pressure state. The axis C represents an axial direction of a joint portion 35. When the negative pressure space S5 enters a negative pressure state, a housing space S2 enters a negative pressure state via the first passage 312, the internal space S3, the second passage 321, and the communication portion S4. In this manner, the breast pump main body 3 generates a negative pressure for sucking the breast milk of the user, i.e., a negative pressure for extracting the breast milk.

The hood 4 is connected to the breast pump main body 3 and placed onto a breast. The hood 4 is formed in the shape of a trumpet or in substantially a dome shape so as to correspond to the shape of the breast, and has a flow path portion 41 and a diameter expansion portion 42. The flow path portion 41 is a part of the hood 4 that has the smallest diameter, and is connected to the mounting portion 311 provided in the breast pump main body 3. Specifically, the flow path portion 41 has a part connected to the breast pump main body 3, and is disposed on the breast pump main body 3 side in the hood 4, i.e., on the back side as seen from an opening 44 of the hood 4. The flow path portion 41 has a cylindrical shape and the inner diameter of the flow path portion 41 is substantially constant. The diameter expansion portion 42 has a corn shape of which a tip of the corn shape is cut off such that a circular hole is formed with a top edge, and is a part that has the diameter thereof expanding from the flow path portion 41 toward an edge portion 43 (or bottom edge) opposite to the flow path portion 41, and the diameter expansion portion 42 is placed onto the breast. The edge portion 43 corresponds to an edge portion of the opening 44 of the hood 4. The diameter of the circular hole is the same as the inner diameter of the flow path portion, and the top edge of the diameter expansion portion 42 is connected to the flow path portion 41. a boundary between the diameter expansion portion and the flow path portion is defined as a boundary portion.

When the user inserts her breast into a space S1 surrounded by the hood 4 shown in FIG. 2, the space S1 creates the housing space S2 for accommodating the nipple of the user so as to seal the nipple of the user. Setting the housing space S2 to a negative pressure creates a structure that enables pumping. At this time, in a state where the breast of the user is in contact with the buffer portion 7 and the diameter expansion portion 42, the nipple of the user enters the flow path portion 41. In other words, the nipple of the user is exposed to the inside of the flow path portion 41. In addition, the areola portion around the nipple is disposed in the vicinity of a boundary portion between the flow path portion 41 and the diameter expansion portion 42 (see FIG. 6).

The buffer portion 7 is in the shape of a ring and is detachably mounted on the hood 4. Specifically, the buffer portion 7 includes a bonding portion 71 and a sealing portion 72, and is fitted and mounted on the edge portion 43 of the hood 4 at the bonding portion 71. The buffer portion 7 may further include a cushion portion 73 and a bending portion 74. The buffer portion 7 is made of a material softer than the material of the hood 4, and therefore has elasticity. For example, the buffer portion 7 is made of an easily deformable material such as silicone rubber, elastomer, or natural rubber, the material being easily brought into close contact with the breast of the user when pumping. For example, in a case where silicone rubber is used as the material of the buffer portion 7, it is preferred that the material of the buffer portion 7 be silicone rubber having a hardness of approximately HS 20 to 80 according to type A durometer in JIS-K 6253 (ISO 7619).

The bonding portion 71 is fitted into the edge portion 43 of the hood 4. Specifically, the bonding portion 71 is provided with a groove portion that can be fitted into the edge portion 43 of the hood 4. By having the edge portion 43 of the hood 4 caught on the groove portion of the bonding portion 71, the bonding portion 71 is attached to the edge portion 43 of the hood 4. The sealing portion 72 is provided on the opposite side of the bonding portion 71. In other words, the bonding portion 71 is provided at one end of the buffer portion 7. As shown in FIG. 2, the sealing portion 72 is brought into close contact with an inner surface 421 of the diameter expansion portion 42 of the hood 4, between the flow path portion 41 of the hood 4 and the edge portion 43 of the hood 4.

Thus, the buffer portion 7 is formed in a trumpet shape or a funnel shape so as to correspond to the inner surface 421 of the diameter expansion portion 42 of the hood 4. At least a part of the buffer portion 7 is in close contact with the inner surface 421 of the diameter expansion portion 42 of the hood 4. The buffer portion 7 has a function of suppressing irritation and pain generated by the diameter expansion portion 42 coming into abutment with the breast of the user, and a function of preventing the negative pressure set in the housing space S2 surrounded by the breast of the user and the hood 4 from leaking from the breast side of the user. The buffer portion 7 is described hereinafter in detail.

As shown in FIG. 2, an opening 313 is formed on the lower side of the internal space S3, and a backflow prevention valve 36 is attached thereto. For example, an on-off valve called duckbill valve is employed as the backflow prevention valve 36 of the present embodiment. However, the backflow prevention valve 36 is not limited to a duckbill valve. The backflow prevention valve 36 efficiently enables the negative pressure state of the housing space S2 by preventing the breast milk and air passing through the opening 313 from flowing back from the bottle 6. The backflow prevention valve 36 is molded integrally using an elastic body such as a synthetic resin, and therefore has flexibility as a whole. Examples of the material of the backflow prevention valve 36 include silicone rubber, elastomer, and natural rubber.

The backflow prevention valve 36 shown in FIG. 2 has a slit 36S at a tip thereof. The slit 36S closes as soon as the negative pressure space S5 enters a negative pressure state. Specifically, when the negative pressure space S5 enters a negative pressure state, the internal space S3 enters a negative pressure state through the communication portion S4 and the second passage 321. As a result, the slit 36S of the backflow prevention valve 36 closes. Consequently, the housing space S2 can enter a negative pressure state via the first passage 312, while the internal space S3 secures high sealability thereof.

Furthermore, in a state where the breast milk accumulates in the backflow prevention valve 36 and the internal space S3, when the negative pressure state of the negative pressure space S5 is removed, the slit 36S of the backflow prevention valve 36 is opened by the volume of the breast milk and the removal of the negative pressure (changing to a constant pressure), guiding the accumulated breast milk to a space $6 inside the bottle 6. As shown in FIG. 2, the breast pump main body 3 has, at a lower end portion thereof, a detachable portion 314 provided so as to be detachable with respect to the bottle 6. The detachable portion 314 is in a dome shape or a cylindrical shape. The space $6 inside the bottle 6 is communicated with the internal space S3 when the backflow prevention valve 36 opens the opening 313.

As shown in FIG. 2, a female screw portion 315 is provided inside the detachable portion 314. On the other hand, a male screw portion 61 is provided on the outside of an upper end portion of the bottle 6. The female screw portion 315 of the detachable portion 314 and the male screw portion 61 of the bottle 6 can be screwed to each other. Note that the bottle 6 may be a special product designed for the breast pump 2 or a baby bottle or the like applicable to the detachable portion 314. In addition, the bottle 6 does not have to be a molded container and may be a bag.

The diaphragm 34 shown in FIG. 2 is a negative pressure generating member for generating a negative pressure. In the present embodiment, the diaphragm 34 is connected to the diaphragm mounting portion 32R provided in the upper portion of the breast pump main body 3. By mounting the diaphragm 34 onto the diaphragm mounting portion 32R, the negative pressure space S5 is formed between the main body 3 and the diaphragm 34.

The diaphragm 34 is formed of a relatively elastic, soft deformable material, that is, a synthetic resin having a hardness of approximately HS 30 to 70 according to type A durometer in JIS-K 6253 (ISO 7619). Examples of the material of the diaphragm 34 include silicone rubber, isoprene rubber, elastomers such as SEBS (styrene-ethylene-butylene-styrene). In the present embodiment, silicone rubber is used as the material of the diaphragm 34.

As shown in FIG. 2, a lower portion of the joint portion 35 is attached to a bottom surface portion 343 of the diaphragm 34, and an upper portion of the same is coupled to the handle 5. The diaphragm 34 is deformed when receiving, at the bottom surface portion 343, the effect of a reciprocating motion of the handle 5 via the joint portion 35. As a result, the bottom surface portion 343 is pulled up by the joint portion 35, changing the space volume of the negative pressure space S5 formed between the bottom surface portion 343 and the upper portion of the breast pump main body 3. Consequently, the diaphragm 34 applies a certain amount of negative pressure to the negative pressure space S5. Specifically, the deformation of the diaphragm 34 results in the negative pressure state of the negative pressure space S5. When the negative pressure space S5 enters the negative pressure state, the air inside the first passage 312 is sucked through the communication portion S4, the second passage 321, and the internal space S3, thereby sucking (extracting) the breast milk.

The joint portion 35 is formed of a material harder than the material of the diaphragm 34. Examples of the material of the joint portion 35 include polypropylene, polycarbonate, polycicloolefin, polyethersulfone, and other synthetic resins. The joint portion 35 has a flat, disk-shaped base portion 351. The base portion 351 is disposed under the bottom surface portion 343 (the negative pressure space S5 side).

Further, the joint portion 35 has a coupling portion 352 protruding upward from the base portion 351 and extending in the shape of an axis. The coupling portion 352 is coupled detachably to the handle 5. Specifically, the coupling portion 352 can be coupled to the handle 5 by being inserted into a through hole (having a diameter smaller than the base portion 351) formed in the middle of the bottom surface portion 343 of the diaphragm 34, and by being exposed above the bottom surface portion 343. When the user pulls up the handle 5 coupled to the coupling portion 352, the base portion 351 pulls up the bottom surface portion 343 of the diaphragm 34. As a result, the diaphragm 34 is deformed, enlarging the negative pressure space S5. Note that the base portion 351 of the present embodiment is disposed without being connected to the bottom surface portion 343, under the bottom surface portion 343 of the diaphragm 34. However, how the base portion 351 is installed is not limited to the foregoing manner. For example, the base portion 351 may be fixed above the bottom surface portion 343.

As shown in FIG. 2, the coupling portion 352 has a first protrusion 353 and a second protrusion 354 arranged side by side along a stretching direction Z of the coupling portion 352. The first protrusion 353 and the second protrusion 354 each protrude radially from a shaft portion of the coupling portion 352. A first engaging portion 355 is provided between the first protrusion 353 and the second protrusion 354. The first engaging portion 355 is a part recessed (groove part) between the first protrusion 353 and the second protrusion 354. Also, a second engaging portion 356 is provided between the second protrusion 354 and the base portion 351. The second engaging portion 356 is a part recessed (groove part) between the second protrusion 354 and the base portion 351.

The holding member 200 is attached to the breast pump main body 3 and provided so as to be rotatable with respect to the breast pump main body 3. When the holding member 200 rotates with respect to the breast pump main body 3, the handle 5 rotates together with the holding member 200 with respect to the breast pump main body 3, as indicated by arrow A3 and arrow A4 shown in FIG. 3. Note, in the breast pump 2 according to the present embodiment, that the holding member 200 does not always have to rotate with respect to the breast pump main body 3. As shown in FIG. 1, the holding member 200 has an attachment portion 400 and an extension portion 323. The attachment portion 400 is sandwiched between the diaphragm mounting portion 32R and a receiving portion 501 and fitted so as to be rotatable with respect to the breast pump main body 3. The extension portion 323 extends from the attachment portion 400, to support the handle 5 in a reciprocable manner.

The handle 5 shown in FIG. 2 is held by the holding member 200 and supported so as to be reciprocable with respect to the extension portion 323 of the holding member 200. Specifically, the handle 5 can reciprocate in the direction of arrows A1 and A2 shown in FIGS. 1 and 2. The handle 5 is detachably coupled to the coupling portion 352 by coming into engagement with the first engaging portion 355 or the second engaging portion 356. Therefore, the position in the stretching direction Z where the handle 5 and the coupling portion 352 are coupled to each other can be changed. Accordingly, the distance at which the handle 5 pulls up the coupling portion 352 can be changed. Thus, the amount of deformation of the diaphragm 34 can be changed. Specifically, as shown in FIG. 2, the first engaging portion 355 and the second engaging portion 356 are formed in the form of steps, away from each other in the stretching direction Z. Thus, the distance at which the handle 5 pulls up the coupling portion 352 can be changed stepwise in accordance with the engagement position between the handle 5 and the engaging portions 355, 356.

The handle 5 has a long shape and, as a whole, is molded using a relatively hard, lightweight synthetic resin. Examples of the material of the handle 5 include polypropylene, polycarbonate, polycicloolefin, and polyethersulfone. The handle 5 has a lift portion 53 disposed above the diaphragm 34 to lift up the diaphragm 34, and a lever portion 52 that is bent from the lift portion 53 and located on a side surface of the breast pump main body 3.

As shown in FIG. 3, the lift portion 53 is provided with a coupled portion 54 that is coupled to the coupling portion 352. The coupled portion 54 has a holding opening 541 for holding a coupling position of the coupling portion 352, and an insertion opening 542 through which the coupling portion 352 is inserted. The holding opening 541 and the insertion opening 542 are spatially connected to each other.

The inner diameter of the holding opening 541 is slightly larger than the outer diameters of the first engaging portion 355 and the second engaging portion 356 shown in FIG. 2, but is smaller than the outer diameters of the first protrusion 353 and the second protrusion 354. On the other hand, the inner diameter of the insertion opening 542 is larger than the outer diameters of the first protrusion 353 and the second protrusion 354 shown in FIG. 2. Therefore, after inserting the coupling portion 352 into the insertion opening 542, the user can position the handle 5 and the coupling portion 352 to each other by sliding the coupling portion 352 toward the holding opening 541 to place the first engaging portion 355 or the second engaging portion 356 in the holding opening 541.

As shown in FIG. 2, the lever portion 52 is formed into the shape of a lever and functions as a handle. A region outside the lever portion 52 corresponds to a region where the user puts her finger FG other than the thumb. That is, an outer surface of the lever portion 52 corresponds to a surface on which the user places the finger FG other than the thumb. The distance between the outer surface of the lever portion 52 on which the user places the finger FG and a recess portion 317 in the breast pump main body 3 on which the user places the thumb TB is the distance that the user can grab, with the breast pump main body 3 sandwiched between the outer surface of the lever portion 52 and the recess portion 317.

When the user holds the hand grabbing the breast pump main body 3, the lever portion 52 is pushed toward the breast pump main body 3 and therefore approaches the breast pump main body 3. Consequently, the handle 5 rotates about an axial direction X of a spindle portion 324 of the holding member 200 (see arrows A5 and A6 in FIG. 2). As a result, the lift portion 53 of the handle 5 lifts up the diaphragm 34 via the joint portion 35. Subsequently, the space volume of the negative pressure space S5 increases, resulting in the negative pressure state. Thus, the housing space S2 enters a negative pressure state via the communication portion S4, the second passage 321, the internal space S3, and the first passage 312. The breast milk is extracted in this manner.

As shown in FIG. 2, the lever portion 52 is curved gradually toward the outside as the lever portion 52 stretches downward from the region where the finger FG is placed. Therefore, a lower end portion 55 of the handle 5 is shaped so as to curl slightly toward the outside. Therefore, in a case where the user brings the lever portion 52 close to the breast pump main body 3, the finger FG can be prevented from being shifted toward the lower side of the handle 5.

Figure 4:
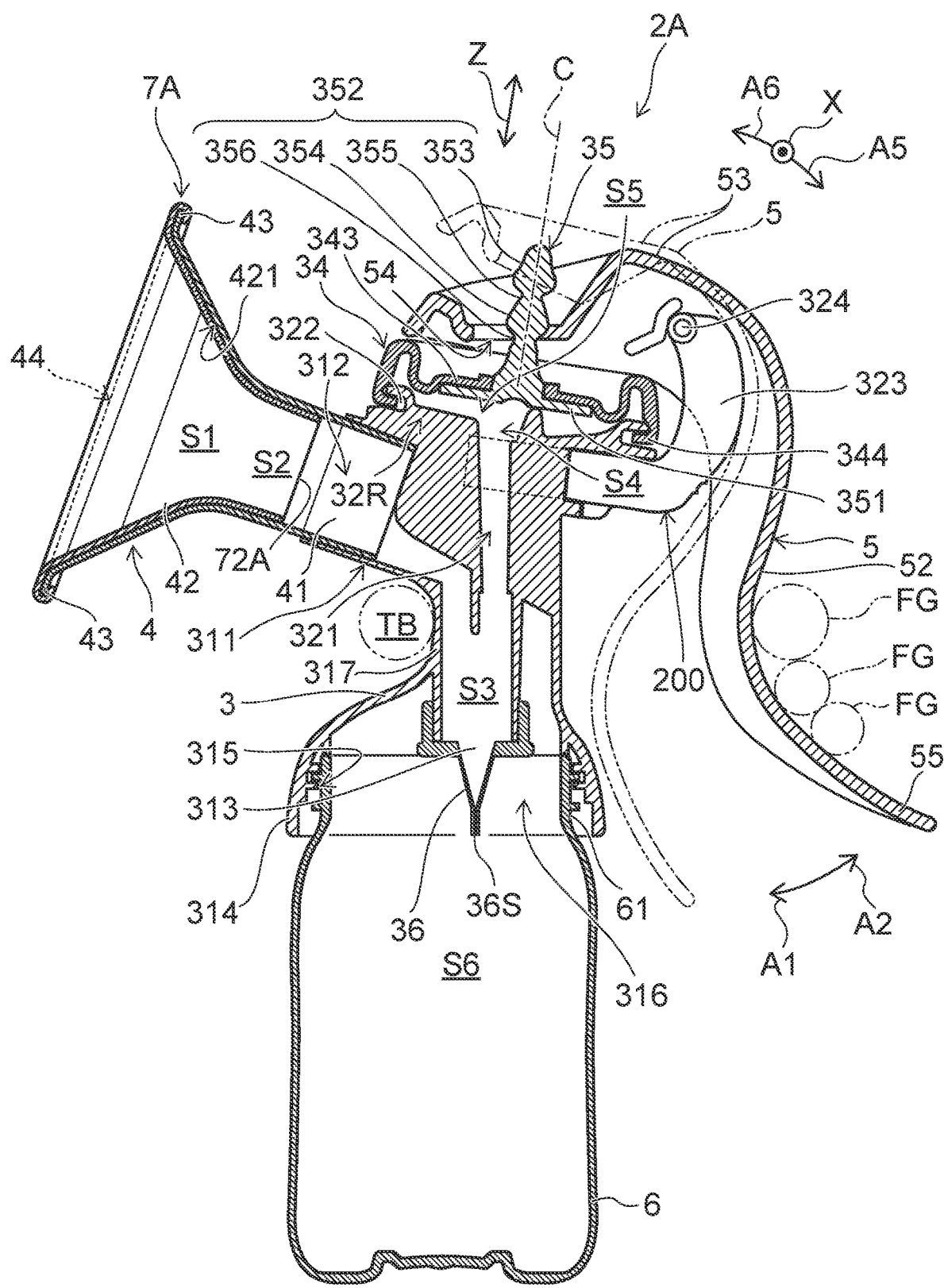
FIG. 4 is a cross-sectional view showing a breast pump according to a comparative example.

A breast pump 2A according to a comparative example is now described with reference to FIG. 4. The breast pump 2A according to the comparative example has the breast pump main body 3, the hood 4, and a buffer portion 7A. The breast pump 2A according to the comparative example may further include the diaphragm 34, the handle 5, the holding member 200, and the bottle 6. In the breast pump 2A according to the comparative example, in a state where the buffer portion 7A is mounted on the hood 4, the buffer portion 7A extends from the edge portion 43 of the hood 4 to the flow path portion 41 of the hood 4. Specifically, in the breast pump 2A according to the comparative example, in a state where the buffer portion 7A is mounted on the hood 4, an end portion 72A opposite to the opening of the buffer portion 7A is disposed in the flow path portion 41 corresponding to the back portion of the hood 4. On the other hand, when the user inserts the breast into the space S1 surrounded by the hood 4, the nipple of the user is positioned in the flow path portion 41. Also, the areola portion of the user is disposed in the vicinity of the boundary portion between the flow path portion 41 and the diameter expansion portion 42. As a result, when inserting the breast into the hood 4, the buffer portion 7A becomes deformed by the negative pressure generated in the housing space S2, and the buffer portion 7A rubs against or pinches the vicinity of the nipple or areola of the user. This cause pain and discomfort to the user at the time of pumping. In addition, in the breast pump 2A according to the comparative example, when the user mounts the buffer portion 7A to the hood 4, a relatively large frictional force may be generated between the buffer portion 7A and the hood 4, and the buffer portion 7A may be caught on the edge portion 43 of the hood 4. As a result, it may take time and effort to mount the buffer portion 7A to the hood 4, or the buffer portion 7A may not be mounted properly onto the hood 4. In a case where the buffer portion 7A cannot properly mounted onto the hood 4, the adhesion of the buffer portion 7A to the hood 4 is reduced, causing the negative pressure generated in the housing space S2 to leak from the breast side of the user.

In contrast, according to the breast pump 2 of the present embodiment, instead of extending from the edge portion 43 of the hood 4 to the flow path portion 41, the buffer portion 7 extends from the edge portion 43 of the hood 4 to a part between the edge portion 43 of the hood 4 and the flow path portion 41 while being mounted to the hood 4. In other words, while the buffer portion 7 is mounted to the hood 4, the sealing portion 72 is positioned on a side of the opening 44 of the hood 4 into which the breast is inserted, as seen from the flow path portion 41 of the hood 4. Specifically, the sealing portion 72 is disposed in the diameter expansion portion 42 between the edge portion 43 and the flow path portion 41, and is in close contact with the inner surface 421 of the diameter expansion portion 42. On the other hand, once the user inserts the breast into the space S1 surrounded by the hood 4 through the opening 44 of the hood 4, the nipple of the user enters the flow path portion 41. Also, the areola portion of the user is positioned in the vicinity of the boundary portion between the flow path portion 41 and the diameter expansion portion 42. Therefore, when inserting the breast into the hood 4 or even when the buffer portion becomes deformed due to the negative pressure generated in the housing space S2 during pumping, the buffer portion 7 can be prevented from rubbing against and pinching the vicinity of the nipple or areola of the user. Thus, the breast pump 2 according to the present embodiment can reduce irritation and pain in the breast of the user.

Furthermore, as described above, instead of extending from the edge portion 43 of the hood 4 to the flow path portion 41, the buffer portion 7 extends from the edge portion 43 of the hood 4 to the part between the edge portion 43 of the hood 4 and the flow path portion 41 while being mounted to the hood 4. Therefore, when the user mounts the buffer portion 7 onto the hood 4, the frictional force generated between the buffer portion 7 and the hood 4 can be reduced, preventing the buffer portion 7 from being caught on the edge portion 43 of the hood 4. Therefore, not only is it possible to mount the buffer portion 7 onto the hood 4 without taking a lot of time and effort, but also improper mounting of the buffer portion 7 onto the hood 4 can be avoided. Thus, the breast pump 2 according to the present embodiment improves the mountability of the buffer portion 7 and prevents the negative pressure generated in the housing space S2 from leaking from the breast side of the user.

The buffer portion and the hood according to the present embodiment are further described next with reference to FIGS. 5 to 7.

Figure 5:
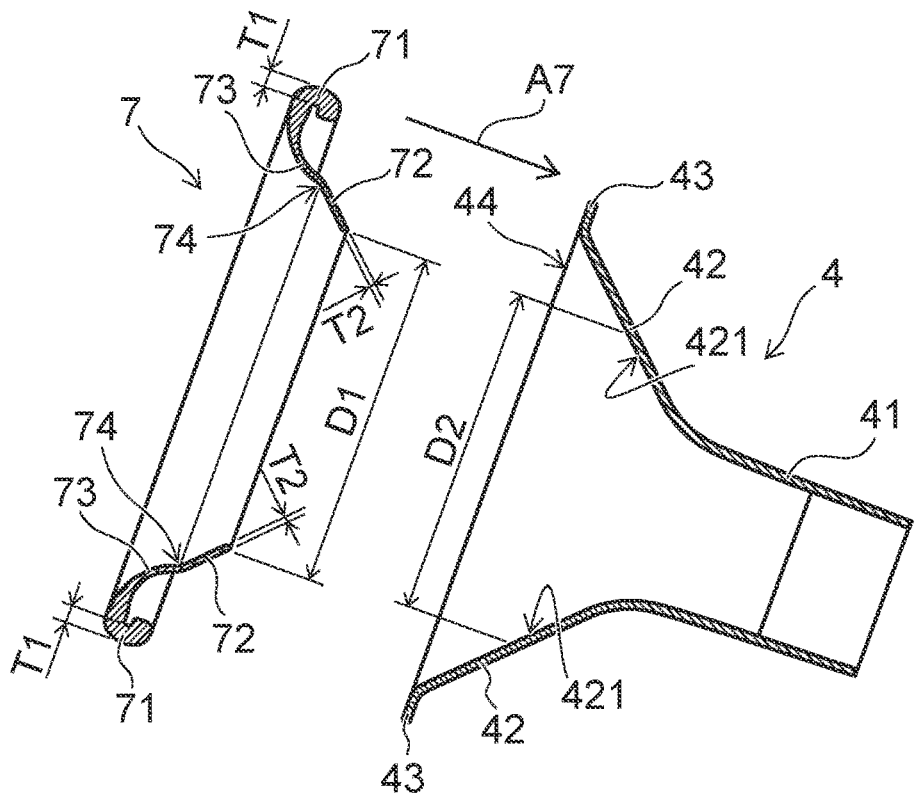
FIG. 5 is a cross-sectional view showing a state obtained prior to mounting a buffer portion of the present embodiment to a hood.
Figure 6:
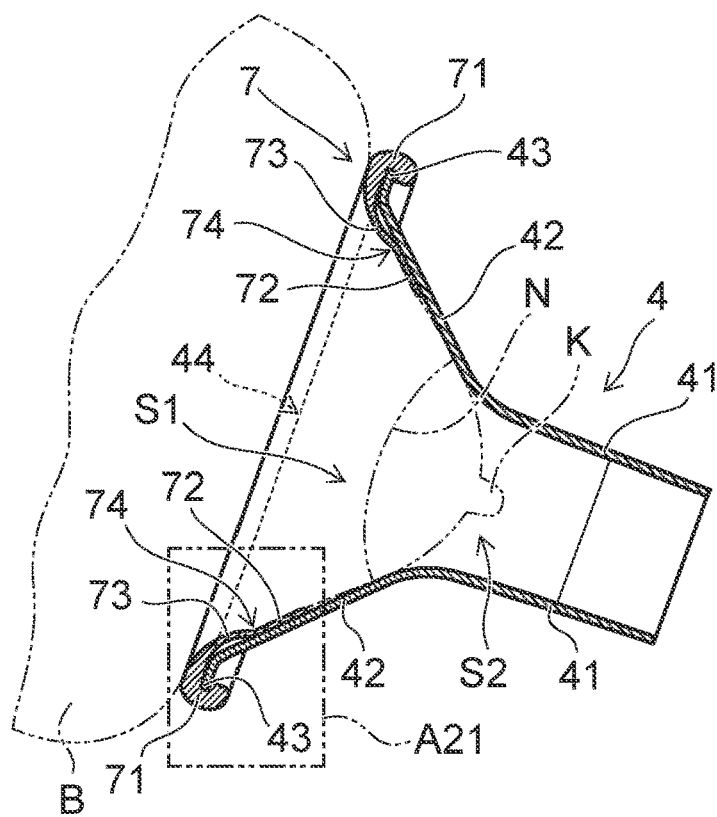
FIG. 6 is a cross-sectional view showing a state obtained after the buffer portion of the present embodiment is mounted onto the hood.

As shown in FIGS. 5 and 6, the buffer portion 7 is mounted detachably onto the hood 4. As indicated by the arrow A7 shown in FIG. 5, the user can mount the buffer portion 7 onto the hood 4 by moving the buffer portion 7 toward the hood 4 and hooking the edge portion 43 of the hood 4 onto the groove portion of the bonding portion 71 of the buffer portion 7. A thickness T1 of the bonding portion 71 is greater than a thickness T2 of the sealing portion 72. Therefore, the rigidity of the bonding portion 71 is higher than the rigidity of the sealing portion 72. According to the buffer portion 7 of the present embodiment, the rigidity of the bonding portion 71 can be enhanced. Consequently, the user can easily mount the buffer portion 7 onto the hood 4.

As shown in FIG. 6, once the user inserts the breast B into the space S1 surrounded by the hood 4 through the opening 44 of the hood 4, the space S1 includes the housing space S2 for accommodating a nipple K of the user in such a manner as to seal the nipple K. At this time, while the breast B of the user is in contact with the buffer portion 7 and the diameter expansion portion 42, the nipple K of the user enters the flow path portion 41. In other words, the nipple K of the user is exposed to the inside of the flow path portion 41. Moreover, an areola portion N around the nipple K is positioned in the vicinity of the boundary portion between the flow path portion 41 and the diameter expansion portion 42.

The sealing portion 72 of the present embodiment is disposed in the diameter expansion portion 42 between the edge portion 43 and the flow path portion 41 such that the leading edge of the sealing portion directs toward the flow path portion and does not reach the boundary portion, and the outer surface of the sealing portion is in close contact with the inner surface 421 of the diameter expansion portion 42. Therefore, when inserting the breast B into the hood 4 or even when the buffer portion 7 becomes deformed by the negative pressure generated in the housing space S2 at the time of pumping, the buffer portion 7 can be prevented from rubbing against or pinching the vicinity of the nipple K or areola portion N of the user. Therefore, the breast pump 2 according to the present embodiment can reduce irritation and pain in the breast B of the user.

As shown in FIG. 5, an outer diameter D1 of a tip (or leading edge) of the sealing portion 72 is slightly larger than an inner diameter D2 of a corresponding part of the diameter expansion portion 42 with which the tip of the sealing portion 72 comes into contact when the buffer portion 7 is mounted on the hood 4.

Figure 7:
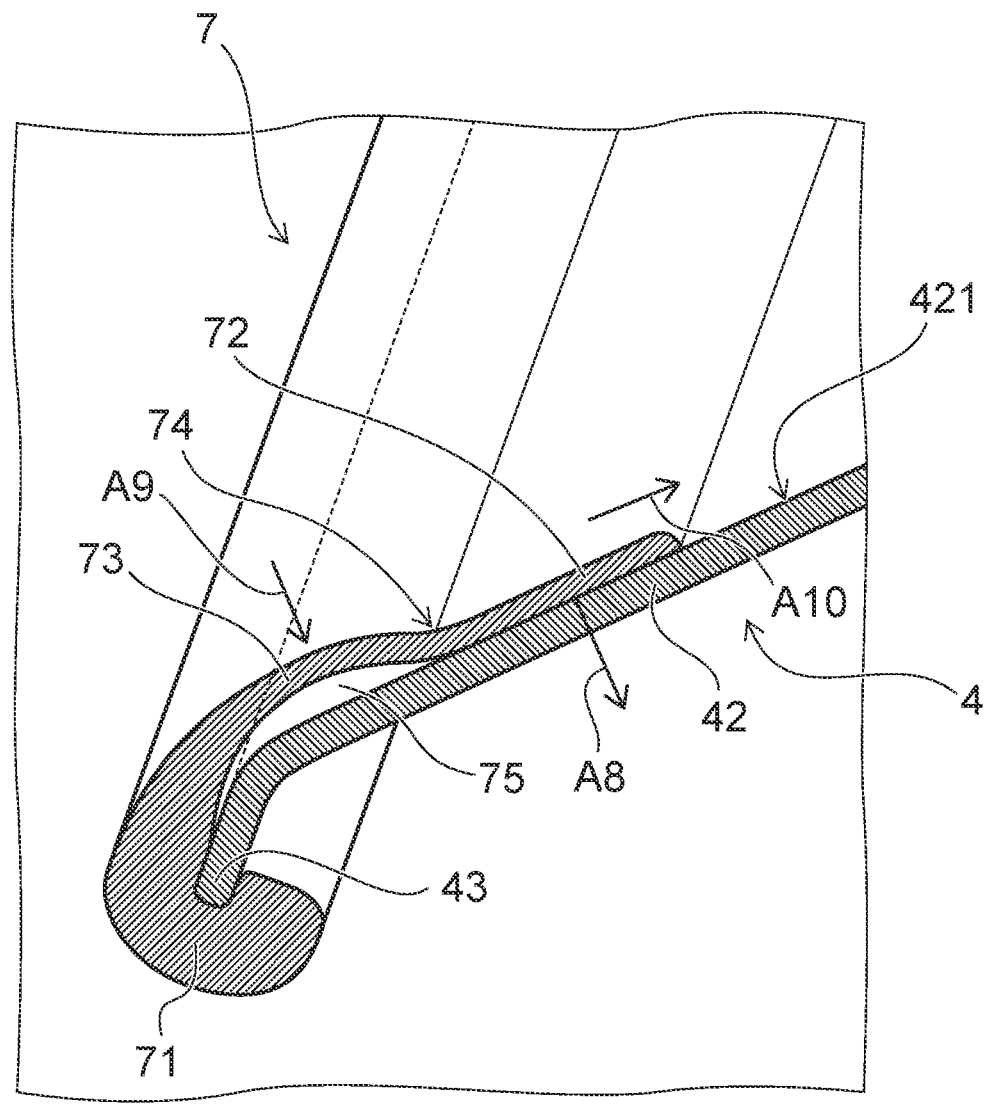
FIG. 7 is an enlarged view of a region A21 of the buffer portion of the present embodiment shown in FIG. 6.

According to this configuration, with the buffer portion 7 mounted on the hood 4, a force in a direction perpendicular to the inner surface 421 of the diameter expansion portion 42 is applied from the sealing portion 72 to the diameter expansion portion 42, as indicated by arrow A8 shown in FIG. 7. Specifically, since the outer diameter D1 of the tip of the sealing portion 72 is larger than the inner diameter D2 of the part of the diameter expansion portion 42 with which the tip of the sealing portion 72 comes into contact, virtually the tip of the sealing portion 72 bites into the part of the diameter expansion portion 42 with which the tip of the sealing portion 72 comes into contact. On the other hand, since the material of the buffer portion 7 is softer than the material of the hood 4, in reality, the tip of the sealing portion 72 cannot bite into the part of the diameter expansion portion 42 with which the tip of the sealing portion 72 comes into contact. Consequently, the tip of the sealing portion 72 tries to deform toward the inside of the diameter expansion portion 42. At this moment, since the buffer portion 7 has elasticity, when the tip of the sealing portion 72 is compressed and tries to deform toward the inside of the diameter expansion portion 42, the force generated inside the tip part of the sealing portion 72 is dispersed throughout the entire tip part of the sealing portion 72. Therefore, the tip portion of the sealing portion 72 can apply the force toward the inner surface 421 of the diameter expansion portion 42, while having the occurrence of wrinkles in the tip part prevented. Consequently, as indicated by the arrow A8 shown in FIG. 7, in the state where the buffer portion 7 mounted on the hood 4, the force in the direction perpendicular to the inner surface 421 of the diameter expansion portion 42 is applied from the sealing portion 72 to the diameter expansion portion 42. As a result, the adhesion between the sealing portion 72 and the diameter expansion portion 42 can be improved, thereby preventing the breast milk from entering between the sealing portion 72 and the diameter expansion portion 42.

As shown in FIG. 7, the buffer portion 7 has the cushion portion 73. The cushion portion 73 is provided on the entire circumference between the bonding portion 71 and the sealing portion 72. The cushion portion 73 protrudes from the diameter expansion portion 42 toward the inside of the diameter expansion portion 42, and is provided in a position away from the inner surface 421 of the diameter expansion portion 42. Therefore, a space 75 is provided between the cushion portion 73 of the buffer portion 7 and the diameter expansion portion 42 of the hood 4. The space 75 can function as an air cushion. The cushion portion 73, therefore, is capable of not only fitting gently to the breast B of the user to ensure comfortable skin contact but also ensuring the airtightness of the space S2 surrounded by the breast B, the buffer portion 7, and the hood 4.

Further, the buffer portion 7 has the bending portion 74. The bending portion 74 is a part provided at a boundary between the cushion portion 73 and the sealing portion 72, and is provided as a folding allowance portion, a folding line portion, or a step portion between the cushion portion 73 and the sealing portion 72. The bending portion 74 bends when the cushion portion 73 is deformed, to prevent the deformation of the cushion portion 73 from being transmitted to the sealing portion 72. Specifically, once the user inserts the breast B into the space S1 surrounded by the hood 4 through the opening 44 of the hood 4, the breast B comes into contact with the cushion portion 73. As described above, the cushion portion 73 gently fits to the breast B of the user as an air cushion portion, to ensure comfortable skin contact. The cushion portion 73 then becomes deformed and collapses, as indicated by arrow A9 shown in FIG. 7. In other words, the space 75 between the cushion portion 73 and the diameter expansion portion 42 collapses. At this moment, the bending portion 74 bends, to prevent the deformation of the cushion portion 73 from being transmitted to the sealing portion 72. In addition, when the cushion portion 73 is deformed and collapses, the bending portion 74 and the sealing portion 72 move (or slide) toward the flow path portion 41 along the inner surface 421 of the diameter expansion portion 42, as indicated by arrow A10 shown in FIG. 7. Specifically, the bending portion 74 and the sealing portion 72 move toward the part of the diameter expansion portion 42 having a smaller inner diameter. Therefore, as compared with the state prior to the deformation and collapse of the cushion portion 73, the force applied to the inner surface 421 of the diameter expansion portion 42 from the bending portion 74 and the sealing portion 72 is increased. Consequently, even when the cushion portion 73 becomes deformed, the bending portion 74 prevents the sealing portion 72 from becoming deformed or from floating from the diameter expansion portion 42, thereby ensuring the adhesion between the sealing portion 72 and the diameter expansion portion 42.

The embodiments of the present invention have been described above. However, the present invention is not limited to the foregoing embodiments, and therefore various modifications can be made without departing from the scope of claims. The configurations of the foregoing embodiments can be partially omitted or arbitrarily combined so as to be different from the foregoing embodiments.

REFERENCE SIGNS LIST 2, 2A Breast pump
3 Breast pump main body
4 Hood
5 Handle
6 Bottle
7, 7A Buffer portion
32R Diaphragm mounting portion
34 Diaphragm
35 Joint portion
36 Backflow prevention valve
36S Slit
41 Flow path portion
42 Diameter expansion portion
43 Edge portion
44 Opening
52 Lever portion
53 Lift portion
54 Coupled portion
55 Lower end portion
61 Male screw portion
71 Bonding portion
72 Sealing portion
72A End portion
73 Cushion portion
74 Bending portion
75 Space
200 Holding member 311 Mounting portion
312 First passage
313 Opening
314 Detachable portion
315 Female screw portion
316 Opening
317 Recess portion
321 Second passage
322 Groove portion
323 Extension portion
324 Spindle portion
343 Bottom surface portion
344 Lower end portion
351 Base portion
352 Coupling portion
353 First protrusion
354 Second protrusion
355 First engaging portion
356 Second engaging portion
400 Attachment portion
421 Inner surface
501 Receiving portion
541 Holding opening
542 Insertion opening
B Breast
C Axis
D1 Outer diameter
D2 Inner diameter
FG Finger
K Nipple
N Areola portion
S1, S2, S3 Space
S4 Communication portion
S5 Space
T1, T2 Thickness
TB Thumb

The invention claimed is:

1. A breast pump, comprising:
a breast pump main body generating a negative pressure for pumping;
a hood connected to the breast pump main body and placed onto a breast; and
a buffer portion having a ring shape and mounted detachably to the hood, the buffer portion being made of a material softer than a material of the hood and having elasticity, wherein
the hood includes:
a flow path portion that has a cylindrical shape of which an inner diameter is substantially consistent, and is connected to the breast pump main body and through which breast milk extracted from the breast passes; and
a diameter expansion portion that has
 a corn shape of which a tip of the corn shape is cut off such that a circular hole is formed with a top edge wherein a diameter of the circular hole is the same as the inner diameter of the flow path portion, the top edge is connected to the flow path portion, and a boundary where the diameter expansion portion and the flow path portion are connected is defined as a boundary portion, and
 an inner diameter expanding from the top edge as approaching toward a bottom edge, which is opposite to the top edge, and
 is configured to be placed onto the breast;
the buffer portion is configured with
 a bonding portion that is provided at one end of the buffer portion and fitted to the edge portion; and
 a sealing portion that is provided on a side of the buffer portion opposite to the bonding portion and of which outer surface comes into close contact with an inner surface of the diameter expansion portion for sealing, wherein a leading edge of the sealing portion directing toward the flow path portion does not reach the boundary portion.

2. The breast pump according to claim 1, wherein
an outer diameter of a tip of the sealing portion is larger than the inner diameter of a part of the diameter expansion portion, the part of the diameter expansion portion coming into contact with the tip of the sealing portion.

3. The breast pump according to claim 2, wherein
the buffer portion further includes a cushion portion which, between the bonding portion and the sealing portion, is positioned away from the inner surface of the diameter expansion portion.

4. The breast pump according to claim 3, wherein the buffer portion further includes a bending portion provided at a boundary between the cushion portion and the sealing portion, the bending portion being configured to bend when the cushion portion is deformed, thereby preventing the deformation of the cushion portion from being transmitted to the sealing portion.

5. The breast pump according to claim 4, wherein a thickness of the bonding portion is greater than a thickness of the sealing portion.

6. The breast pump according to claim 3, wherein a thickness of the bonding portion is greater than a thickness of the sealing portion.

7. The breast pump according to claim 2, wherein a thickness of the bonding portion is greater than a thickness of the sealing portion.

8. The breast pump according to claim 1, wherein
the buffer portion further includes a cushion portion which, between the bonding portion and the sealing portion, has a curved shape in a cross-sectional view and is positioned away from the inner surface of the diameter expansion portion such that a space is created between the cushion portion and the diameter expansion portion.

9. The breast pump according to claim 8, wherein the buffer portion further includes a folding line provided at a boundary between the cushion portion and the sealing portion such that the boundary between the cushion portion and the sealing portion is configured to bend when the cushion portion is deformed, thereby preventing the deformation of the cushion portion from being transmitted to the sealing portion.

10. The breast pump according to claim 9, wherein a thickness of the bonding portion is greater than a thickness of the sealing portion.

11. The breast pump according to claim 9, wherein
an outer diameter of the leading edge of the sealing portion is slightly larger than an inner diameter of a corresponding part of the diameter expansion portion wherein the corresponding part corresponds to the leading edge of the sealing portion in the cross-sectional view when the buffer portion is mounted on the hood, and
when the cushion portion is deformed, the sealing portion and the folding line are configured to slide toward the flow path portion along the inner surface of the diameter expansion portion.

12. The breast pump according to claim 8, wherein a thickness of the bonding portion is greater than a thickness of the sealing portion.

13. The breast pump according to claim 8, wherein
an outer diameter of the leading edge of the sealing portion is slightly larger than an inner diameter of a corresponding part of the diameter expansion portion wherein the corresponding part corresponds to the leading edge of the sealing portion in the cross-sectional view when the buffer portion is mounted on the hood, and when the cushion portion is deformed, the sealing portion is configured to slide toward the flow path portion along the inner surface of the diameter expansion portion.

14. The breast pump according to claim 8, wherein
the sealing portion is positioned away from the boundary portion not to allow an areola portion of a user to touch the sealing portion when the hood is placed onto the breast of the user.

15. The breast pump according to claim 8, wherein
the outer surface of the sealing portion is entirely in contact with the inner surface of the diameter expansion portion.

16. The breast pump according to claim 1, wherein a thickness of the bonding portion is greater than a thickness of the sealing portion.

\* \* \* \* \*